United States Patent [19]

Fearon et al.

[11] 3,997,787
[45] Dec. 14, 1976

[54] APPARATUS AND METHOD FOR DETECTING EXPLOSIVES

[75] Inventors: Robert E. Fearon, Tulsa, Okla.; Serge A. Scherbatskoy, Fort Worth, Tex.

[73] Assignee: Bain Griffith, Birmingham, Mich.

[22] Filed: Apr. 25, 1975

[21] Appl. No.: 571,702

[52] U.S. Cl. .......................... 250/359; 250/492 R; 250/494; 250/499
[51] Int. Cl.² ........................................ G01M 23/00
[58] Field of Search .......... 250/303, 312, 358, 359, 250/363, 367, 499, 500, 492 R, 494

[56] References Cited
UNITED STATES PATENTS

| | | | |
|---|---|---|---|
| 3,146,349 | 8/1964 | Jordan | 250/391 |
| 3,255,352 | 6/1966 | Johnston | 250/303 |
| 3,808,444 | 4/1974 | Schneeberger et al. | 250/358 |
| 3,832,545 | 8/1974 | Bartko | 250/359 |
| 3,878,373 | 4/1975 | Blum | 250/303 |

*Primary Examiner*—Harold A. Dixon
*Attorney, Agent, or Firm*—Stevens, Davis, Miller & Mosher

[57] ABSTRACT

Apparatus and method for detecting the presence of nitrogen and oxygen-containing explosives within a container by irradiating the container with thermal and high energy neutrons, and then measuring the quantity of thermal energy neutrons passing through the container and the quantity of radioactive nitrogen 16 generated within the container. The measurements of neutron absorption and nitrogen 16 are correlated to provide an output signal indicative of whether the material within the container is an explosive.

17 Claims, 8 Drawing Figures

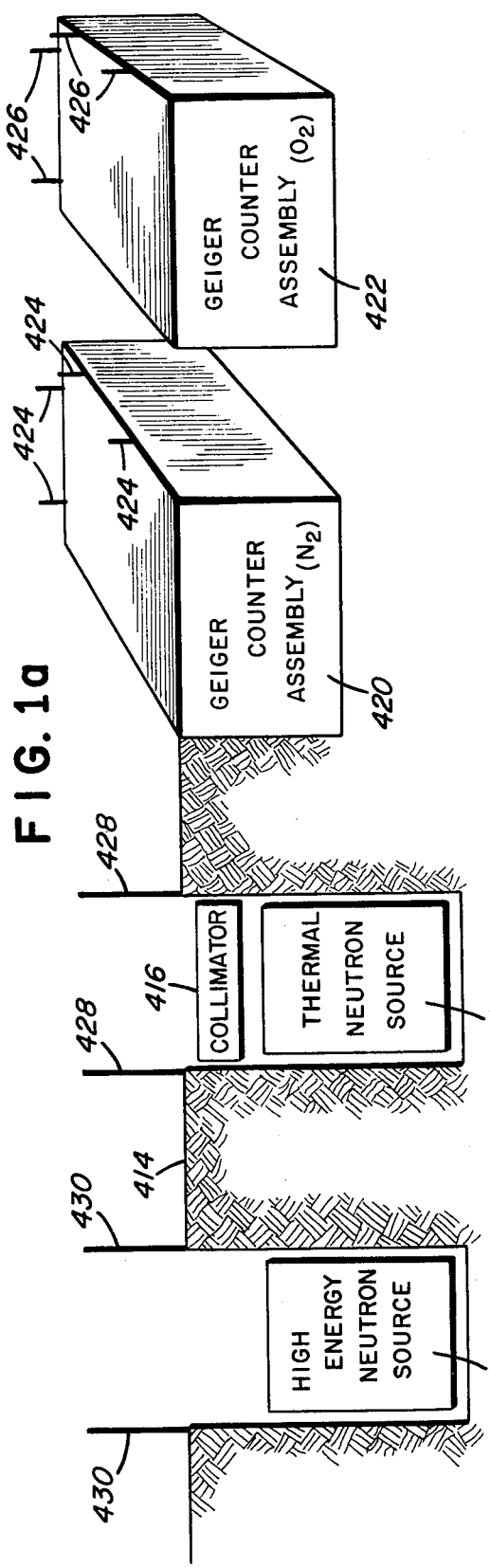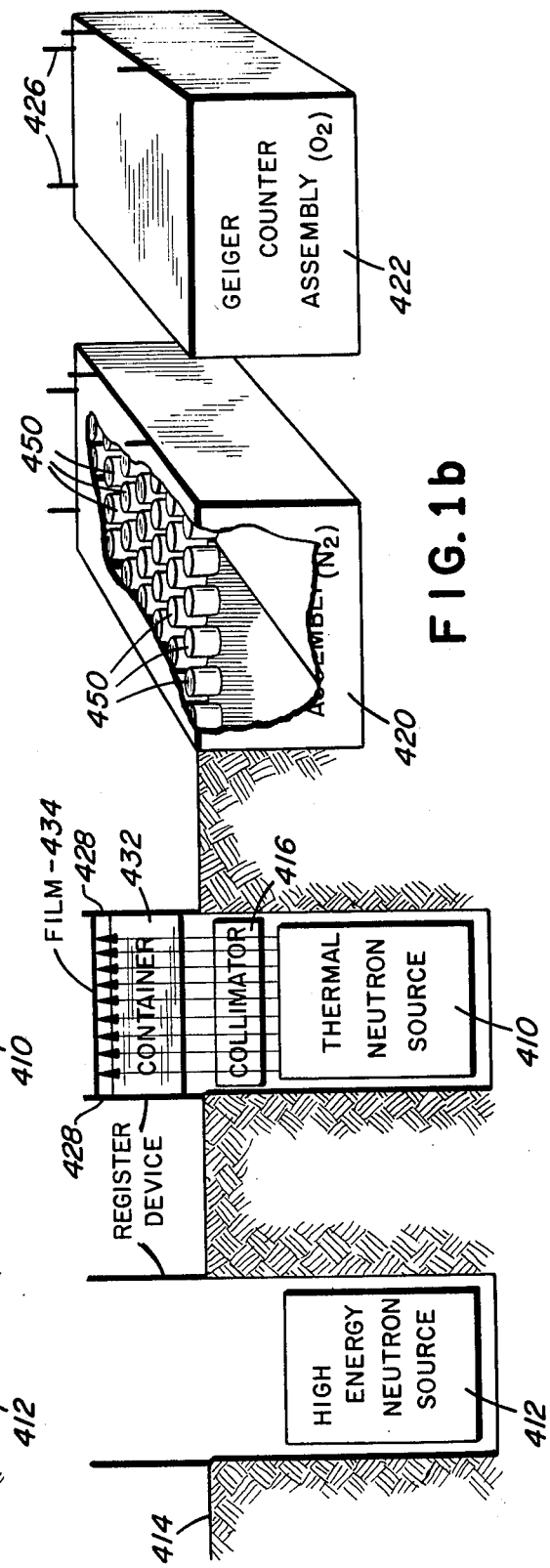

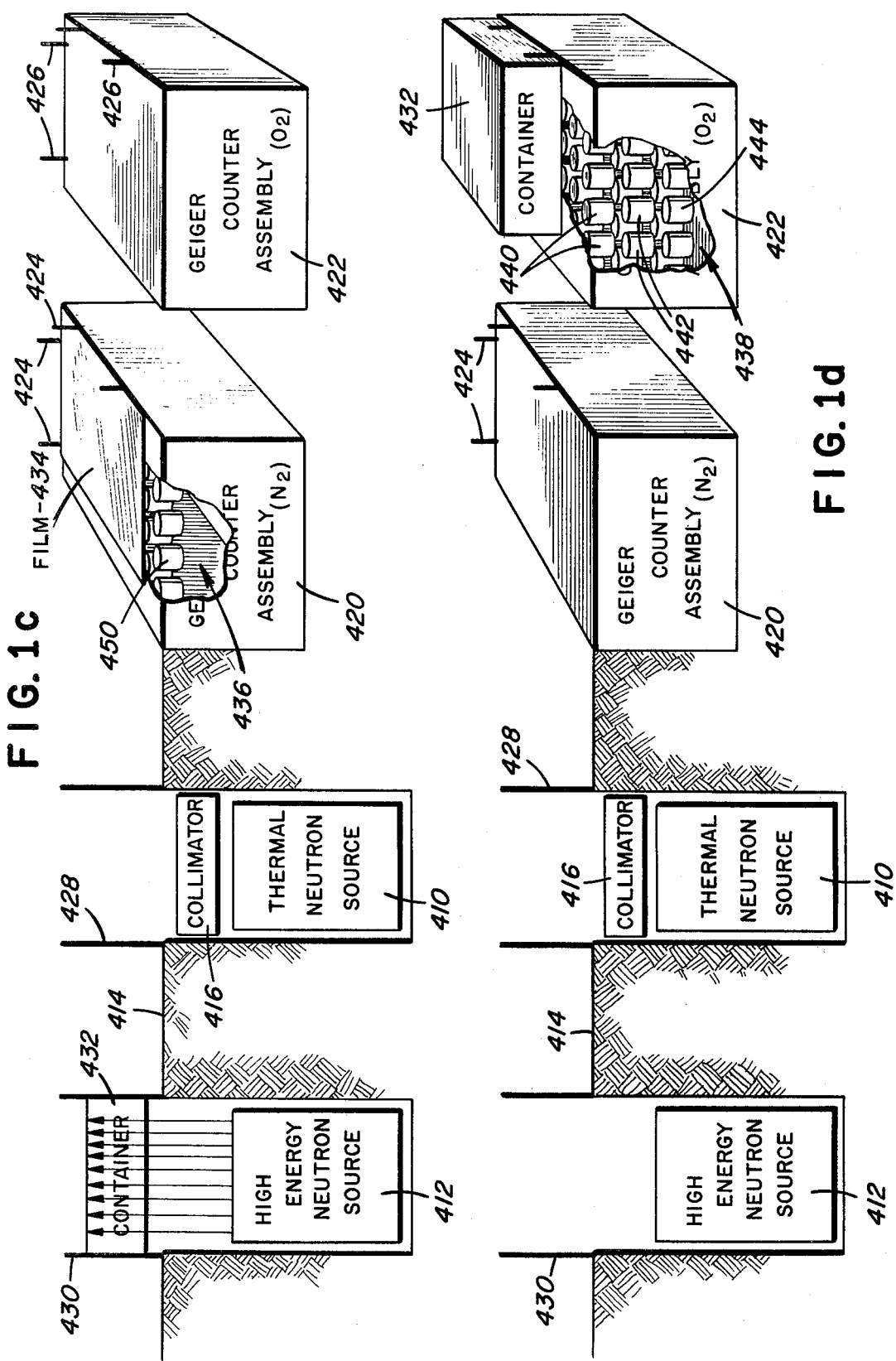

APPARATUS AND METHOD FOR DETECTING EXPLOSIVES

BACKGROUND OF THE INVENTION

This invention relates to an apparatus and method for detecting, measuring and correlating the oxygen and nitrogen content of a substance within an enclosed space and, in particular, for determining, with a high probability, whether such substance is an explosive.

There has been an increasing incidence of violent behavior throughout the world and this behavior has sometimes manifested itself by the placing of explosives in packages which are then sent through the mails or placed aboard aircraft. An urgent need exists for the better protection of Post Office employees, aircraft crews, passengers and others who may be killed or injured by the detonation of explosives. Explosives in aircraft baggage presents a particular hazard since their detonation while the aircraft is in the air is almost always catastrophic and such detonation may be caused by a change in pressure or temperature, time or by a radio or supersonic signal.

All modern explosives of which we are aware contain a relatively large amount of both nitrogen and oxygen, sufficient oxygen being required to very nearly oxidize all the carbon and hydrogen in the explosive. Examples of such explosives are nitroglycerin, sensitized nitromethane, trinitrotoluene, penterythritol tetranitrate, nitrocellulose, cyclonite, nitrostarch, nitrosugar and nitromannitol. Therefore, the detection of the presence of nitrogen and oxygen in high concentrations may be indicative of the presence of a bomb. More specifically, if a very high concentration of the element nitrogen is found in a suitcase or other enclosure where there is also a very high concentration of the element oxygen, there is a high probability the suitcase contains an explosive. Further, there are certain shapes which are more probable for bombs. Generally, the shape of a bomb is substantially cylindrical, the cylinder being several times as long as the distance across its base. A bundle of sticks of dynamite or nitroglycerine gelatins may be somewhat irregular in shape but, as a rule, it will be compact and located in only one part of the suitcase with the other contents of the suitcase distributed around the perimeter of the dynamite package. Compact shapes are usually necessary or the bomb may not explode in its entirety.

There are a number of non-explosive substances which have characteristics in common with explosive materials. These include cheese, leather, after shave lotion and acrylic plastics. For example, cheese contains nitrogen and, because of the moisture in it, has oxygen in combination with hydrogen in the form of water. In the pyrolysis of cheese the products obtained include water vapor, ammonia and amines, combustible organic vapors, elemental carbon and a relatively small amount of elemental nitrogen in gaseous form. On the other hand, nitroglycerine, the essential basis of many commonly available explosives, has different properties. Exploding under substantially ideal conditions, two moles of nitroglycerine yield three moles of diatomic nitrogen gas, six moles of carbon dioxide, five moles of water vapor, and half a mole of diatomic gaseous elemental oxygen in addition to a very large number of calories of heat energy.

Comparing cheese with nitroglycerine, it is seen that they differ not only in that the cheese won't explode, but in the fact that the explosive has a much higher population of nitrogen atoms per unit volume and concurrently a very high population of oxygen atoms in the same volume as compared to that in the same volume of cheese. With regard to after shave lotion, the glass in the bottle contains a large number of oxygen atoms per unit volume as does the enclosed liquid but it does not contain any nitrogen. The acrylic plastic has less oxygen and no nitrogen. Polyurethane plastics have nitrogen and oxygen but their total amount is far less than that of an explosive and, in particular, the amount of oxygen is less in the polyurethane plastic.

SUMMARY OF THE INVENTION

We have invented an apparatus and method which may be used to detect, measure and correlate the oxygen and nitrogen contents of a substance located within an enclosed space. This apparatus and method may, in particular, be used to determine with high probability whether a substance located within such a space constitutes an explosive. As a specific example, the apparatus might be used to examine each piece of luggage before it is placed aboard an aircraft without the necessity of opening the luggage. The most common form of luggage is a suitcase in which one of the dimensions is very much less than the other two; thus, suitcases can be treated in an approximation as though they are a flat sheet of material. In accordance with our invention, an image is formed showing the area density of nitrogen and oxygen within the suitcase while, at the same time, providing a visual indication of the relative amounts of nitrogen and oxygen. In this way, luggage which the apparatus indicates may contain an explosive substance can be isolated and searched without the necessity of opening all pieces of luggage being shipped. The apparatus also provides means for adjusting the threshold of sensitivity so that the probability of detecting an explosive package is increased although this may at the same time increase the percentage of non-explosive containing suitcases which are detected by the apparatus.

In carrying out our method of determining whether an enclosure includes substances having oxygen or nitrogen in amounts exceeding predetermined amounts, the enclosure is first irradiated with thermal energy neutrons; that is, neutrons having energies in the approximate range 0.01 to 0.10 electron volt per neutron. The quantity of thermal energy neutrons which pass through the enclosure is then measured to obtain an indication corresponding to the amount of neutron absorbing material including nitrogen within the enclosure. This may be done by placing a layer of indium or silver foil above the suitcase for a suitable period, removing the foil and then measuring the quantity of beta ray emission from the foil by a mosaic detection device.

The enclosure is next irradiated with higher energy neutrons having energies in excess of $10.6 \times 10^6$ electron volts per neutron to transform the oxygen within the enclosure to radioactive nitrogen of atomic weight 16. The enclosure is then removed from the high energy neutron source and the quantity of radioactive nitrogen 16 within the enclosure measured to obtain an indication corresponding to the amount of oxygen within the enclosure. The beta ray emission, which is proportional to the amount of neutron absorbing material within the enclosure (corresponding substantially to its nitrogen content), and the signal proportional to the quantity of radioactive nitrogen 16 within the enclosure (corresponding to the amount of oxygen therein) are correlated to provide an indication whenever the combined amounts of nitrogen and oxygen indicate a high probability that the enclosure contains an explosive. In addition, a display device may be employed to provide a two-dimensional image showing the distribution of areas containing amounts of oxygen and nitrogen sufficient to trigger the device.

While the above description relates particularly to the detection of nitrogen and oxygen within a container by the use of thermal and high energy neutrons, it will be understood that other substances may also be detected and that other forms of radiation may be employed.

BRIEF DESCRIPTION OF THE DRAWINGS

FIGS. 1(a) – 1(d) are schematic diagrams showing the steps in determining the oxygen and nitrogen content of materials contained within an enclosure such as a suitcase.

DESCRIPTION OF THE PREFERRED EMBODIMENTS

Figure 2:
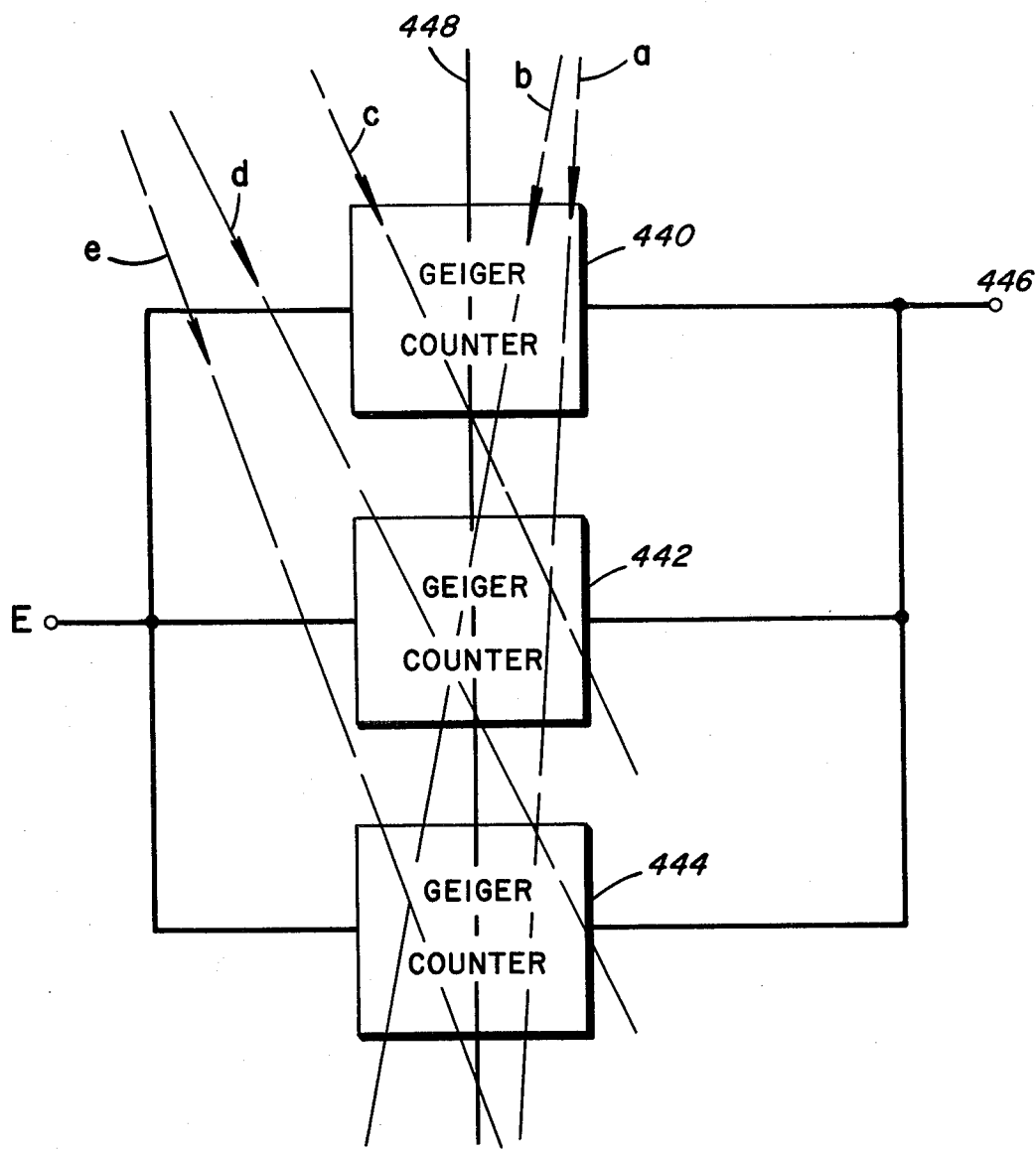
FIG. 2 is a schematic diagram showing a three Geiger counter unit for detecting the presence of oxygen within the suitcase.

Referring to FIG. 1(a), there is shown an explosive detection installation in which a thermal neutron source 410 and a high energy neutron source 412 are located below the ground level 414. The thermal neutron source 410 can be of any type capable of emitting neutrons in the approximate range 0.01 to 0.10 electron volt per neutron but is preferably a reactor of the "pickle barrel" type. Such reactors are also known as "small subcritical low powered reactors" normally having a neutron reproduction ratio (K) of about 0.99. A suitable primary neutron source is used to turn on the reactor, and this source may be a spontaneous fission source containing californium, radium beryllium, actinium beryllium or polonium beryllium. While all of these primary sources will operate satisfactorily, a radium beryllium encapsulated preparation is preferred because its neutron emission exhibits long term constancy. To compensate for the relatively feeble output of the preferred primary source, the K factor of the pickle barrel may be adjusted quite close to unity and damping rods included to maintain the K factor at a value just under unity.

At the time the reactor is placed below ground, boron and/or a rare earth material is installed permanently in the reactor to control its K factor to a value which is just barely subcritical. This is done to make certain total withdrawal of the control rods will not produce a sustained chain reaction. The reactor is surrounded with a layer of paraffin or water (not shown) approximately 1 foot thick which contain a quantity of boron (borax, boric oxide, element boron). In the event the reactor is not installed below ground, a wall containing gamma ray absorbing materials is also needed. For a moderate radiation intensity, a foot of concrete in which the aggregate is comprised of hermatite or magnetite is sufficient.

For the below-ground installation shown in FIG. 1(a), an upward extending concrete parapet may be employed. The parapet has openings at least as large as a typical suitcase and a basin (not shown) affording approximately 15 centimeters of water, paraffin, petroleum oil or other hydrogen rich material is placed within the parapet. Immediately above the water basin there is provided a collimator 416 in the form of a thick layer (for example, ten inches) of polyethylene in which, dispersed as a filler, is disposed a quantity of finely powdered borax glass. The layer of polyethylene is provided with a pattern of large holes approximately one inch in diameter drilled perpendicularly therethrough, the holes extending vertically, and the 10-inch slab lying horizontally above the water basin. The effect of the system of holes is to produce a flux of slow neutrons having the characteristics of a substantially parallel beam. Details of the pickle barrel reactor primary neutrons source and water basin have not been shown in FIG. 1(a) since these elements are known in the art and do not comprise our invention. A "pickle barrel" reactor is described in the "Proceedings of the University Subcritical Assemblies Conference," L. B. Borst, TID-7619 Reactor Technology, DTIE issuance date January 1961.

The high energy neutron source 412 which employs the deuterium-tritium reaction emits neutrons having energies in excess of $10.6 \times 10^6$ electron volts per neutron. These neutrons have a kinetic energy in substantial excess of the threshold for the reaction $^{16}O$—(n,p)-$^{16}N^*$ where n and p designate a neutron and proton respectively and the asterisk means that the resulting nitrogen isotope is radioactive, in this instance having a half-life of about 7.4 seconds. Approximately 26 percent of the disintegrations of the radioactive nitrogen produced from oxygen by this bombardment correspond with high energy electrons of a group having a maximum energy of $10.44 \times 10^6$ electron volts and many of the electrons of this energy distribution are of sufficiently high velocity that they can be expected to easily penetrate the walls of a piece of luggage. In fact, the maximum energy electrons of this group are twenty times as massive as an electron at rest and, therefore, proceed generally in a straight line through absorbing material until considerably slowed down. Also, the range of such electrons in air is very high and the electrons of this energy are deflected very little in passage through a few inches of air. Further, heavy material such as lead or iron may be employed to guide the electron radiation thereby providing an excellent means for determining, within reasonable limits, the place of origin of an electron counted by a counter situated at the inside end of a long narrow opening in the mass of iron or lead.

As is well-known, neutrons being generated on a target of a deuterium-tritium reactor all come from a very small spot on the target, very much as is the case with the emission of x-rays from the target in the x-ray tube. To a first approximation, the neutron source 412 is effectively a point, when considered in comparison to the dimensions of the enclosure. Neutrons diverge from such a source, becoming less concentrated the further from the source one observes their intensity. There is a degree of anisotropy in their emission, more being emitted transverse to the original direction of the bombarding deuterons. At a distance, nevertheless, the radiation from such a source appears substantially uniform and parallel. A suitcase supported appropriately above the high energy neutron source may therefore be regarded as receiving an equal bombardment with the high energy neutrons over its entire exposure area.

Geiger counter enclosures 420 and 422 are located adjacent the neutron sources 410 and 412 and are provided with restraining members 424 and 426 for proper positioning of a suitcase, luggage or other container placed above them. Registration devices 428 and 430 are also provided above the neutron sources 410 and 412 respectively so that a container having contents to be analyzed may be accurately positioned within the neutron beams.

Referring to FIG. 1(b), a container 432 has been placed between the registration devices 428 above thermal neutron source 410 and collimator 416 for radiation with thermal energy neutrons. Container 432 may be any enclosure whose contents in general cannot be seen, such as a package, suitcase or other luggage. Immediately above container 432 is placed a layer of indium foil 434 which is kept in position for a period of about 10 seconds during operation of the thermal neutron source. The foil 434 is then removed from above the container 432 and placed over Geiger counter enclosure 420, as shown in FIG. 1(c). Enclosure 420 is provided with a horizontal single level of Geiger counters 436 distributed, for example, in a 20 × 20 array of 400 counters. The indium foil 434 is kept in position above the array 436 for about 10 seconds and then removed. As will be described hereinafter, the outputs of the counters 436 provide an indication of the relative amount and locations of nitrogen containing substances within the container.

An indium film is employed because its 53 minute half-life permits deliberate handling and allows sufficient time to make a panorama of the nitrogen content within the container 432. This half-life also permits increase in the exposure time of the indium beyond 10 seconds if necessary without increasing the radiation intensity. Where greater sensitivity is required, a silver film having a 13 second half-life may be used but scanning is more difficult because of the rapid decay of the activated silver.

The panorama obtained from the beta ray emission of film 434 corresponds to the zones of neutron absorption (thermal neutrons) within the container 432. Nitrogen, among the common elements, is unusual in its relatively high absorption of thermal neutrons, the absorption coefficient varying inversely with the velocity $v$ of the neutrons. Other substances which strongly absorb thermal neutrons are very rare in the earth in terms of their cosmic abundance and are also uncommon in articles used by man. Cadmium, for instance, exhibits strong absorption of thermal neutrons but the absorption is banded and does not obey the $1/v$ law. In fact, some slightly epithermal neutrons are readily passed by cadmium. Boron has a neutron absorption characteristic generally similar to that of nitrogen and the element gadolinium has a very high neutron absorption quality as do many of the other rare earths. Thus, it is seen that articles commonly found in suitcase belonging to the ordinary traveler are not at all likely to look like bombs in terms of their neutron absorption.

While the beta ray emission from film 434 is being measured by the array of Geiger counters 436, the container 432 is transferred by mechanical means (not shown) to a position above the high energy neutron source 412. The source 412 then bombards the container with a flux of neutrons derived from the deuterium-tritium reaction for a period of about 5 seconds. This bombardment converts the oxygen in the container to radioactive nitrogen by the reaction previously described.

The container is then quickly removed to a location away from that at which the activation was performed, preferably within one to two seconds, and placed on the Geiger counter enclosure 422 having Geiger counters 438 arranged in three spaced coplanar 20 × 20 groups of 400 counters each, each group of 400 counters being in registration with the other groups to form 400 sets of counters spaced along axes perpendicular to the planes of the counter groups. As in the case of the Geiger counters in enclosure 420, the choice of 400 counters per coplanar group is only typical and more or fewer counters may be used in different array patterns. Mechanical apparatus required for moving the container 432 from the high energy neutron source 412 to the Geiger counter enclosure 422 has not been shown since apparatus of this type is well known. Further, if desired, the three-level array 438 may be mechanically substituted for the single level array 436 in enclosure 420 for each measurement rather than employing two separate enclosures.

FIG. 2 illustrates diagrammatically a set of three Geiger counters 440, 442 and 444 which comprise a single vertical row in the three-level array of the oxygen detecting Geiger counter enclosure 422 shown in FIG. 1(d). Radiation from the container 432 impinges on the top of enclosure 422 and strikes the counters in the order 440, 442 and 444. That is, the nature of the spatial sequence is such that an electron moving with a kinetic energy in excess of $5 \times 10^6$ electron volts can easily pass through the walls of every counter of the sequence, provided it is travelling initially in a direction which will produce a path that intercepts each of the three counters.

The output of each of the counters consists of a sequence of impulses, each impulse being responsive to the passage of a charged particle through the atmosphere in the interior of the counter. The current waveform at the output of one of the Geiger counters is such that the current rises extremely abruptly at the beginning of each impulse but then disappears more slowly as the impulse terminates. Further, the impulses which are generated at the output of each Geiger counter are, within very narrow limits, equal in magnitude regardless of the nature of the charged particles producing the impulses. The reason for the equality of the impulses is the space charge cloud of slowly moving positive ions which terminate the discharge. Space charge clouds cluster around the anode, which is a fine wire in the case of a typical Geiger counter.

A counter which is useful in the present application is disclosed in U.S. Pat. No. 2,886,713 granted May 12, 1959. This counter, which can work at very high voltages and is not affected by the small sparks that are likely to occur in the air, operates with an anode voltage E between 2,000 and 3,000 volts and with a resistance in series with the voltage source of about 1 megohm. Good Geiger counter performance is achieved under such conditions, the impulses being extremely steep on the front side and substantially equal in magnitude independent of the particles which produced them.

Because of the counter arrangement shown in FIG. 2, the signal at the output terminal 446 is made up of electrical impulses of three distinct kinds: first, those impulses in which only one of the counters has been energized by a nuclear radiation particle; second, impulses approximately twice the size of the usual impulse which occur every time two of the counters are fired simultaneously; and third, impulses having three times the magnitude of the impulse of the single counter and occurs when all three counters are energized by the same particle. In FIG. 2, dashed lines $a$ and $b$ represent the path of particles which intercept the three counters 440, 442 and 444, line $c$ represents particles which intercept two of the counters 440 and 442, $d$ the path of a particle which intercepts two counters 442 and 444 and $e$ the path of a particle which intercepts only one counter 444.

By the use of a threshold circuit to be discussed hereinafter, the system can be arranged so that only those particles which are intercepted by all three counters 440, 442 and 444 operate the system. In this way, the system responds only to radiation which is close to the vertical axis 448 of the three-counter set and therefore is not affected by background radiation not originating within the container 432. The background count, when present, adds to the measurement but more importantly contributes random variations due to the statistical uncertainty associated with the background itself. Conveniently, the large majority of background count processes are not such that they would affect adjoining counters at the same time and are extremely unlikely to affect two other nearby counters simultaneously. Therefore, through the use of a triple coincidence arrangement, a counting procedure is achieved which is sensitive only to the radiation processes that are properly directed and have sufficient energy. The improvement of the statistics of the measurement is a consequence of the absence of background count in the triple coincidence arrangement.

Figure 3:
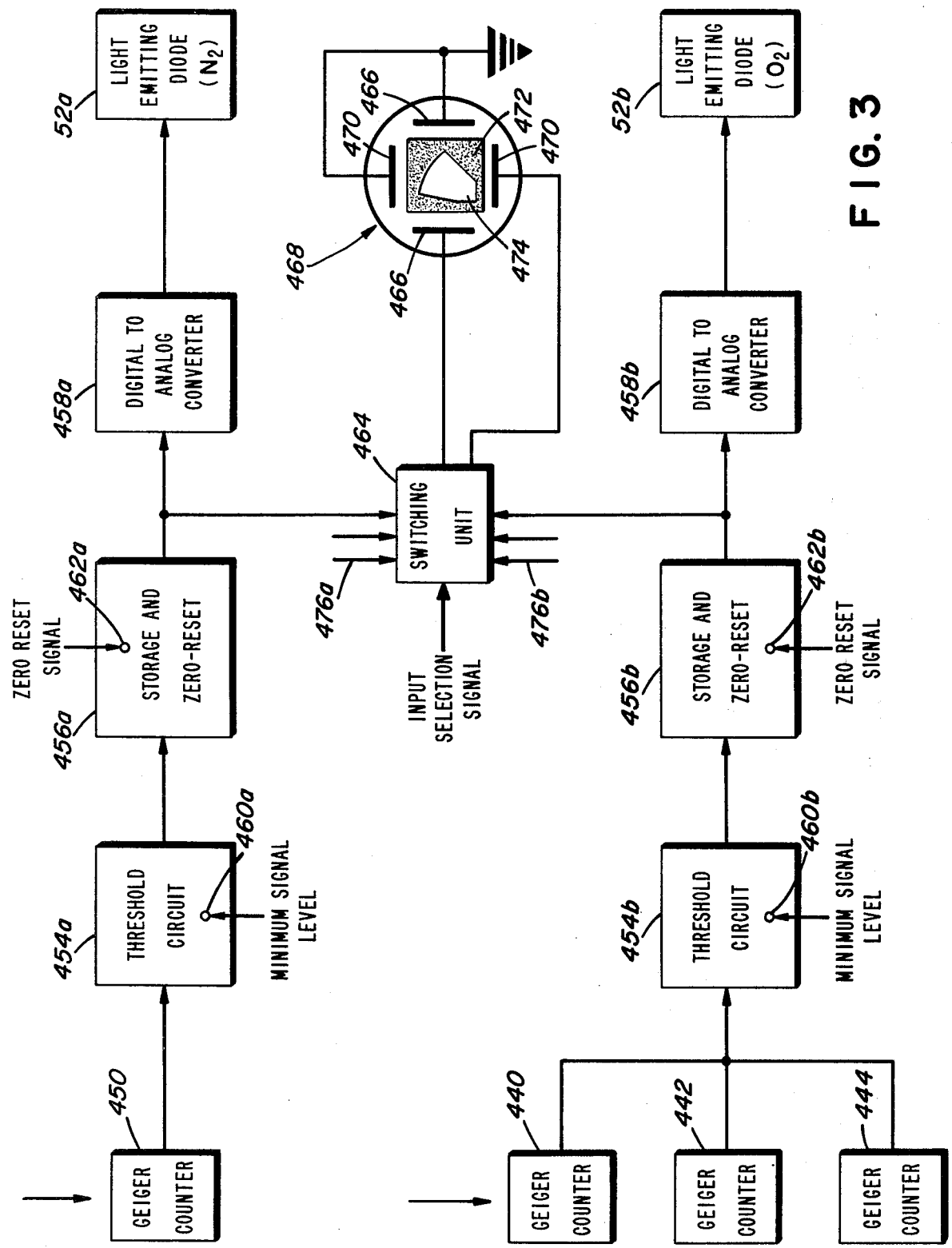
FIG. 3 is a block diagram showing one unit of a system for indicating the presence of nitrogen and oxygen within the suitcase.

FIG. 3 is a block diagram of the components employed in a single unit of our system for detecting explosives. All of the components shown in FIG. 3, with the exception of the switching unit 464 and cathode ray oscilloscope 468 are required for each of the counters in the array 436 and for each set of three counters in the array 438. Thus, in a system employing 400 counters in the array 436 and 1200 counters in the array 438, a total of 400 of the units shown in FIG. 3 (except switching unit 464 and oscilloscope 468) are required. Integrated circuits and large-scale integration techniques are used to minimize cost and space requirements.

In FIG. 3, Geiger counter 450 is illustrative of one of the 400 counters in the array 436 of FIG. 1($b$). Counter 450 energizes a light emitting diode 52$a$ through a threshold circuit 454$a$, a storage and zero-reset circuit 456$a$ and a digital-to-analog converter 458$a$. Each of the other 399 Geiger counters in the array 436 are connected through an identical circuit to a corresponding light emitting diode.

Similarly, the parallel outputs of Geiger counters 440, 442 and 444 of array 438 are connected through a threshold circuit 454$b$, a storage and zero circuit 456$b$ and a digital-to-analog converter 458$b$ to a light emitting diode 52$b$. Identical circuits are provided for each of the other 399 three-level arrays of FIG. 1($d$) and each group of counters is coupled to a corresponding light emitting diode.

Figure 4:
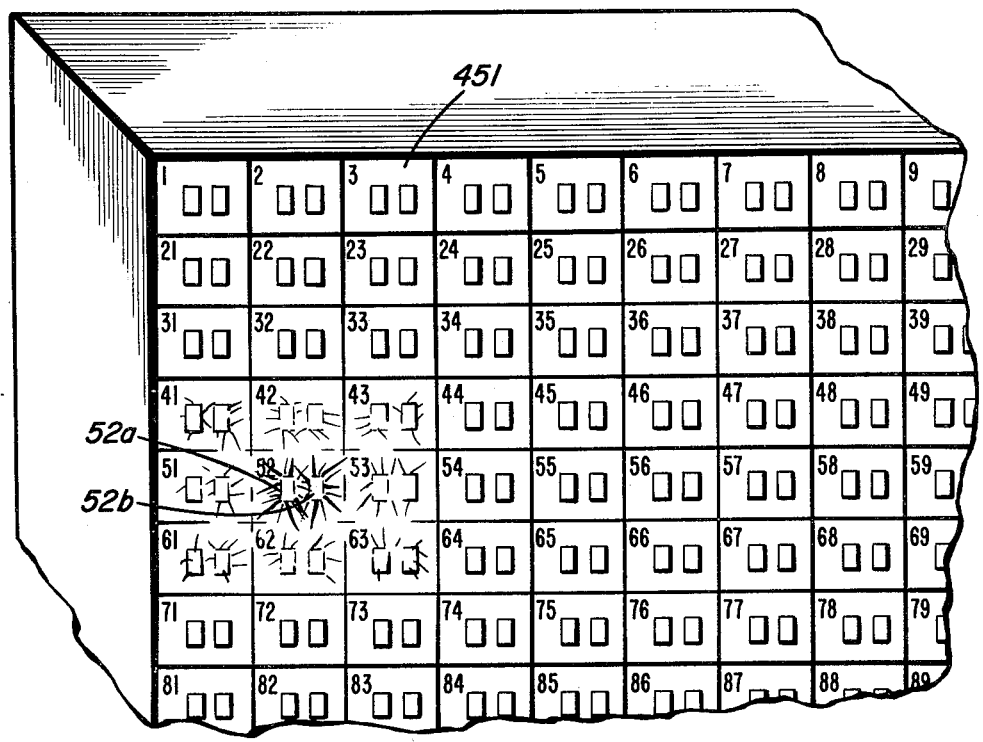
FIG. 4 is a partial front view of a display panel for indicating the presence of predetermined amounts of oxygen and nitrogen within the suitcase.

Referring to FIG. 4, there is shown a part of a display panel or screen 451 which is viewed by the operator of the explosive detecting equipment. The screen is divided into squares numbered from 1 to 400, each number corresponding to a Geiger counter in the array 436 and a corresponding set of three counters in the array 438. Two light emitting diodes are located in each of the numbered squares. Illumination of both diodes in a square indicates that the portion of the container 432 which caused the corresponding Geiger counters to be irradiated contains substances having sufficient nitrogen and oxygen to exceed the minimum signal level set at inputs 460$a$ and 460$b$ of threshold circuits 454$a$ and 454$b$ and, therefore, may contain an explosive substance. For example, if light emitting diodes 52$a$ and 52$b$ located in square 52 of the screen 51 are both emitting light, this is an indication relatively large amounts of oxygen and nitrogen are present within the counter at a location which irradiates counters 450 and 440, 442, 444. Further, the greater the brightness of the light emitted by the diodes and the larger the number of squares in which both diodes emit light, the greater the possibility the suitcase or luggage being tested contains an explosive. In a typical instance, if a relatively small explosive device were hidden in a suitcase the diodes in several adjacent squares would emit light while the diodes in the other squares of the display screen 51 would be dark. Thus, in FIG. 4 the diodes in squares 41 – 43, 51 – 53 and 61 – 63 are shown as emitting light indicating that an explosive containing device may be present in the corresponding location of suitcase 32.

More specifically, Geiger counter 450 receives radiation from an incremental area of indium film 434 which has been irradiated by an incremental volume of the container 432. This radiation, which corresponds to the amount of nitrogen in the incremental volume of the container, produces a signal at the output of the counter 450 which is applied to threshold circuit 454$a$. If the signal received from the counter 450 exceeds a minimum magnitude set into the threshold circuit 454$a$ at input 460$a$, an output voltage is generated which is coupled to the storage and reset circuit 456$a$. Circuit 456$a$ stores the pulses received from counter 450 through threshold circuit 454$a$ for a predetermined period of time, or reset interval, established by a zero-reset signal applied to terminal 462$a$. The total count stored in the storage circuit 456$a$ is converted from digital-to-analog form in D-to-A converter 458$a$ and applied to light emitting diode 52$a$. Thus, diode 52$a$ emits light having a brightness corresponding to the sum of those pulses generated by counter 450 during the reset interval which exceed the threshold signal applied to threshold circuit 454$a$. Consequently, the brightness of the light emitted by diode 52$a$ corresponds to the amount of nitrogen in the corresponding volume of the container 432.

Similarly, Geiger counters 440, 442 and 444 receive radiation from the container 432 after it has been irradiated with high energy neutrons from source 412. In a preferred embodiment, the threshold circuit 454$b$ is set to pass only signals having a magnitude large enough to indicate that the radiation passed through all three counters 440, 442 and 444 and not to respond to radiation which, because of its direction with respect to the vertical axis 448 of the counters, passes through only one or two of the counters. The operation of storage and reset circuit 456$b$ and D-to-A converter 458$b$ is the same as that of circuits 456a and 458a and produces light emission from diode 52b which corresponds to the amount of oxygen in the corresponding volume of container 32.

A switching unit 464 is connected to the outputs of storage and reset circuits 456a and 456b for connecting the output of circuit 456a across the horizontal deflecting plates 466 of a cathode ray tube 468 and the output of circuit 456b across the vertical deflecting plates 470 of the CRT. Thus, a horizontal deflection of the CRT beam is a measure of the amount of nitrogen in a specific volume of container 432 and the vertical deflection is a measure of the amount of oxygen in that volume of the container. A mask 472 having a cutout area 474 is placed over the face of cathode ray tube 468 so that a signal is displayed in the cutout portion 494 only when there is a high probability an explosive is located within the container being examined. The other inputs to the switching unit 464, as for example inputs 476a and 476b, are connected to identical circuits provided for energizing the other light emitting diodes in screen 451 by their corresponding Geiger counters.

The threshold circuits 454a, 454b, storage reset circuits 456a, 456b and digital-to-analog converters 458a, 458b are preferably digital integrated circuits available commercially from manufacturers of integrated circuits. Alternatively, analog devices may be used to provide the threshold and storage functions. The light emitting diodes are also available commercially and may, if desired, emit light of different colors, for example, red and green, to identify nitrogen and oxygen respectively. The light from each pair of diodes can be combined to provide a single indication that an item of luggage contains a substance having an appreciable amount of nitrogen and oxygen.

Figure 5:
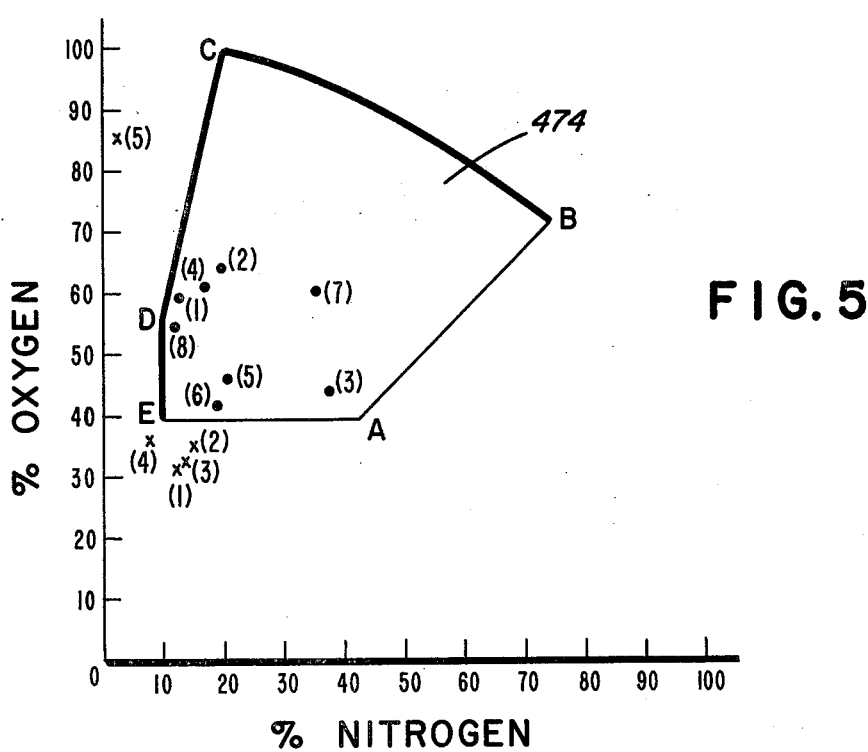
FIG. 5 is an enlarged view of the cathode ray tube of FIG. 3 showing a mask for correlating nitrogen and oxygen data.

FIG. 5 is an enlarged view of the face plate of cathode ray tube 468 showing the mask 472 and the beam deflections obtained when substances having different amounts of nitrogen and oxygen are located within container 432. The shape of the mask, as designated by the letters A, B, C, D and E, is determined by the oxygen-nitrogen ratios which it has been established are indicative of an explosive composition. In FIG. 5, the dots falling within the mask area 474 show the positions assumed by the electron beam of the CRT when the luggage 432 being examined contains the known explosives listed in Table A and the crosses falling outside the mask area ABCDE designate the position of the electron beam for the non-explosives listed in Table B.

TABLE A

COMPOSITIONS OF EXPLOSIVES

| Explosive | | % Carbon | % Hydrogen | % Oxygen | % Nitrogen |
|---|---|---|---|---|---|
| Nitrocellulose (97% Nitration) | (1) | 24.8 | 2.5 | 59.0 | 13.7 |
| Nitroglycerin | (2) | 15.9 | 2.2 | 63.4 | 19.5 |
| RDX | (3) | 16.3 | 2.7 | 43.2 | 37.8 |
| PETN | (4) | 19.0 | 2.5 | 60.76 | 17.72 |
| Tetryl | (5) | 30.8 | 1.8 | 46.9 | 20.5 |
| TNT | (6) | 37.0 | 2.2 | 42.3 | 18.5 |
| Ammonium Nitrate | (7) | 0 | 5 | 60 | 35 |
| Ammonium Perchlorate* | (8) | 0 | 3.4 | 54.4 | 12 |

*Chlorine - 35.5%

TABLE B

NON-EXPLOSIVE SUBSTANCES CONTAINING NITROGEN AND OXYGEN

| Substance | | % Carbon | % Hydrogen | % Oxygen | % Nitrogen | % Sulphur |
|---|---|---|---|---|---|---|
| Casein | (1) | 48.2 | 7.5 | 31.0 | 12.7 | .6 |
| Gelatin | (2) | 42.7 | 7.1 | 35.0 | 15.0 | .2 |
| Egg Albumin | (3) | 42.6 | 6.7 | 32.7 | 13.8 | 4.2 |
| Mono-Sodium Glutinate* | (4) | 35.5 | 4.7 | 37.9 | 8.3 | 0 |
| Household Ammonia (3% NH₃) | (5) | 0 | 11.3 | 86.2 | 2.5 | 0 |

*13.6 % Sodium

In operation, if both light emitting diodes in any given square of the display panel 451 shown in FIG. 4 are illuminated, the operator actuates the switching unit 464 so that the outputs of the corresponding storage and zero-reset circuits for that square are connected to the CRT 468. If a lighted spot appears within the closed area ABCDE, the container being examined would then be subject to further scrutiny to determine whether it contains explosives. On the other hand, if no indication is observed because the electron beam is displaced to a point outside the area 474, this indicates that the oxygen-nitrogen content is such that the material within the container 432 is not an explosive and further investigation is unnecessary.

Table A shows the compositions of some common explosives and, in particular, their oxygen and nitrogen content. Table B provides similar information for common non-explosive substances which contain nitrogen and oxygen, the oxygen and nitrogen contents of each of the materials listed in Tables A and B being plotted on FIG. 5. For example, ammonium nitrate, containing about 60 percent oxygen and 35 percent nitrogen, would cause both the nitrogen and oxygen indicating light emitting diodes in display panel 468 to fall near the center of the exposed area 474 of the mask as shown by the dot labelled (7). This would indicate to the operator of the explosive detecting equipment that there is a high probability luggage being examined contains an explosive and security forces would be alerted.

On the other hand, luggage containing 3 percent household ammonia with about 86.2 percent oxygen and 2.5 percent nitrogen would cause the light emitting diodes connected to Geiger counter array 436 to radiate brightly and the light emitting diodes connected to Geiger counter array 438 to glow only dimly or not at all depending upon the setting of the corresponding threshold circuits. Confirmation that the luggage did not contain an explosive could be obtained by connecting the CRT by means of switching unit 464 to the outputs of the storage circuits associated with one or more of the light emitting diodes providing the radiation noted by the operator. In the case of household ammonia, the electron beam would fall on the tube outside the open mask area 474 at the cross labelled (5) and, therefore, the operator would not see it and would conclude properly that the luggage did not contain an explosive. It would also be possible to make the mask 472 of translucent rather than opaque material so that a more positive indication that the substance in the luggage being examined is non-explosive could be obtained.

It will be understood that the shape of the mask is determined by the materials of interest and an evaluation of the amount of risk which can reasonably be assumed that an explosive may not be detected. The safest system, of course, would be one which detects all substances containing both oxygen and nitrogen but such system would be impractical since almost all luggage travelling through an airport contains some materials which have both of these elements. On the other hand, a mask set to provide very few false alarms may permit a container in which explosives have been placed to pass through the system undetected. Therefore, a practical system may be less than 100 percent safe but will provide a high probability that explosive-containing materials will be detected.

What is claimed is:

1. A method of detecting the presence of a substance within a container, which substance contains at least first and second component materials in amounts exceeding predetermined amounts, comprising the steps of:
   a. irradiating said container with energy of a first kind,
   b. measuring the quantity of said first kind of energy passing through said container to obtain an indication corresponding to the amount of said first component material within said container,
   c. storing said indication,
   d. irradiating said container with energy of a second kind for transferring said second component material to a radioactive material,
   e. removing said container from the source of said second kind of energy,
   f. measuring the quantity of radioactive material within said container to obtain an indication corresponding to the amount of said second component material within said container, and
   g. correlating said indications of the amounts of said first and second component materials to provide an output signal.

2. The method defined by claim 1 wherein said first kind of energy comprises thermal energy neutrons and said second kind of energy comprises neutrons having energies in excess of $10.6 \times 10^6$ electron volts per neutron.

3. A method of detecting the presence of a substance located within a container, which substance includes oxygen and nitrogen in amounts exceeding predetermined amounts comprising:
   a. irradiating said container with thermal energy neutrons,
   b. measuring the quantity of said thermal energy neutrons passing through said container to obtain an indication corresponding to the amount of neutron absorbing material including nitrogen within said container,
   c. storing said indication,
   d. irradiating said container with higher energy neutrons having energies in excess of $10.6 \times 10^6$ electron volts per neutron to transform the oxygen within said container to radioactive nitrogen of atomic weight 16,
   e. removing said container from the source of higher energy neutrons,
   f. measuring the quantity of said radioactive nitrogen 16 within said containers to obtain an indication corresponding to the amount of oxygen within said container, and
   g. correlating said indications of nitrogen and oxygen to provide an output signal.

4. The method defined by claim 3 wherein the step of measuring the quantity of thermal energy neutrons passing through the container comprises placing a film adjacent said container while said container is being irradiated by said thermal energy neutrons, said container being located between the source of said neutrons and said film; and placing said film adjacent a first array of Geiger counters to obtain an output corresponding to the beta ray emission from said film.

5. The method defined by claim 3 wherein the step of measuring the quantity of radioactive nitrogen 16 within said container comprises placing said container adjacent a second array of Geiger counters, said second array of counters including a plurality of sets of counters, each of said sets comprising at least two axially spaced counters; and eliminating from the outputs of each set of counters all signals produced by high energy neutrons not intercepted by all of the axially spaced counters in said set of counters.

6. The method defined by claim 3 wherein the step of measuring the quantity of thermal energy neutrons passing through the container comprises placing a film adjacent said container while said container is being irradiated by said thermal energy neutrons, said container being located between the source of said neutrons and said film; and placing said film adjacent a first array of Geiger counters to obtain an output corresponding to the beta ray emission from said film, and wherein the steps of measuring the quantity of radioactive nitrogen 16 within said container comprises placing said container adjacent a second array of Geiger counters, said second array of counters including a plurality of sets of counters, each of said sets comprising at least two axially spaced counters; and eliminating from the outputs of each set of counters all signals produced by high energy neutrons not intercepted by all of the axially spaced counters in said set of counters.

7. The method defined by claim 3 wherein said thermal energy neutrons have energies in the range 0.01 to 0.10 electron volt per neutron.

8. Apparatus for detecting the presence of a substance within a container, which substance contains oxygen and nitrogen in amounts exceeding predetermined amounts comprising:
   a. a thermal energy neutron source for irradiating said container with thermal energy neutrons,
   b. a high energy neutron source for transforming oxygen within said container to radioactive nitrogen of atomic weight 16,
   c. means for positioning said container in the path of energy emitted by said thermal and high energy neutron sources respectively, d. first measuring means for measuring the quantity of thermal energy neutrons passing through said container, e. second measuring means for measuring the quantity of radioactive nitrogen 16 within said container, and f. means coupled to said first and second measuring means for correlating the outputs of said means for measuring the quantity of thermal energy neutrons passing through said container and said means for measuring the quantity of radioactive nitrogen 16 within said enclosure to obtain indications of the amount of neutron absorbing material including nitrogen within the container and the amount of oxygen with said container.

9. The apparatus defined by claim 8 wherein said means for measuring the quantity of thermal energy neutrons passing through said container comprises a film positioned adjacent said container, said container being located between said thermal energy neutron source and said film; and a first Geiger counter array for obtaining an output corresponding to the beta ray emission from said film.

10. The apparatus defined by claim 9 wherein said film is made of indium.

11. The apparatus defined by claim 8 wherein said means for measuring the quantity of radioactive nitrogen 16 within said container comprises a second Geiger counter array, said second Geiger counter array comprising at least two coplanar groups of counters positioned in registration to form a plurality of sets of counters spaced along axes perpendicular to the planes of said groups of counters, the output of the counters in each set being connected to a common output terminal.

12. The apparatus defined by claim 11 wherein said Geiger counter array comprises three coplanar groups of counters.

13. The apparatus defined by claim 8 wherein said correlating means comprises:

a. first and second threshold means coupled to said first and second measuring means respectively, said first and second threshold means producing output signals only when said first and second measuring means have outputs exceeding predetermined magnitudes, b. first and second storage means coupled to the outputs of said first and second threshold means respectively for storing said threshold output signals, and c. display means coupled to the output of said first and second storage means respectively for displaying the amounts of nitrogen and oxygen in the substance located within said container.

14. The apparatus defined by claim 13 wherein said display means comprises a cathode ray tube having its first and second deflection plates coupled to the outputs of said first and second storage means respectively, the position of the electron beams of said cathode ray tube providing an indication corresponding to the relative amounts of nitrogen and oxygen within said container.

15. The apparatus defined by claim 14 wherein said cathode ray tube is provided with a mask having an aperture therein for displaying only predetermined positions of said electron beam.

16. The apparatus defined by claim 13 wherein said display means comprises first and second light emitting diodes coupled to the outputs of said first and second storage means respectively, said first and second diodes emitting light when the outputs of said first and second measuring means exceed respectively said predetermined threshold magnitudes.

17. The apparatus defined by claim 13 wherein said display means comprises a cathode ray tube having its first and second deflection plates coupled to the outputs of said first and second storage means respectively, the position of the electron beams of said cathode ray tube providing an indication corresponding to the relative amounts of nitrogen and oxygen within said container, and first and second light emitting diodes coupled to the outputs of said first and second storage means respectively, said first and second diodes emitting light when the outputs of said first and second measuring means exceed respectively said predetermined threshold magnitudes.

* * * * *

UNITED STATES PATENT AND TRADEMARK OFFICE
CERTIFICATE OF CORRECTION

PATENT NO. : 3,997,787
DATED : December 14th, 1976
INVENTOR(S) : Robert E. Fearon and Serge A. Scherbatskoy It is certified that error appears in the above-identified patent and that said Letters Patent are hereby corrected as shown below:

Column 12, line 35, change "neutrons" to --electrons--.

Signed and Sealed this

Twenty-sixth Day of June 1979

[SEAL]

Attest:

RUTH C. MASON
Attesting Officer

DONALD W. BANNER
Commissioner of Patents and Trademarks